United States Patent [19]  [11]  4,202,817
Guddal et al.  [45]  May 13, 1980

[54] PROCESS FOR THE PRODUCTION OF PENAM AND CEPHEM DERIVATIVES

[75] Inventors: Erling Guddal, Skovlunde; Poul Borrevang, Rødovre, both of Denmark

[73] Assignee: Novo Industri A/S, Denmark

[21] Appl. No.: 943,463

[22] Filed: Sep. 18, 1978

Related U.S. Application Data

[63] Continuation of Ser. No. 813,246, Jul. 6, 1977, abandoned.

[30] Foreign Application Priority Data

Jul. 7, 1976 [GB] United Kingdom ............... 28346/76

[51] Int. Cl.$^2$ ................... C07D 499/12; C07D 501/06
[52] U.S. Cl. .................................... 260/239.1; 544/26; 544/23; 544/30; 260/245.2 R
[58] Field of Search ...................... 260/239.1, 306.7 E; 544/16, 22, 30

[56] References Cited

U.S. PATENT DOCUMENTS 3,994,883  11/1976  Borrevang et al. ........... 260/239.1 X

OTHER PUBLICATIONS

Lucas et al., J. Am. Chem. Soc. vol. 72, pp. 5491–5497 (1950).
Chemical Abstracts, vol. 47, col. 10, 464(g) (1953).

Primary Examiner—Norman Morgenstern
Assistant Examiner—Vera C. Clarke
Attorney, Agent, or Firm—Watson, Cole, Grindle & Watson

[57] ABSTRACT

A process for the preparation of penam and cephem derivatives by reacting a phosphite amide of a 6-aminopenicillanic acid or 7-aminocephalosporanic acid with an acyl halide in an aprotic solvent in the presence of a phosphite halide scavenger.

13 Claims, No Drawings

PROCESS FOR THE PRODUCTION OF PENAM AND CEPHEM DERIVATIVES

This is a continuation, division, of application Ser. No. 813,246 filed July 6, 1977, now abandoned.

BACKGROUND OF THE INVENTION

This invention relates to a process for the preparation of penam and cephem derivatives by reacting a phosphite amide of the general formula:

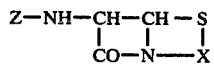  (I), wherein X represents a group of the general formula:

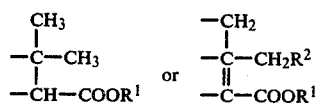

wherein the carbon atom adjacent to the $COOR^1$ group is connected to the nitrogen atom, $R^1$ represents a substituted or non-substituted alkyl or aralkyl group, or a metal organic group, $R^2$ represents hydrogen, an acetoxy group, or —S—Het, wherein Het represents a heterocyclic group, and Z represents a group having the formula:

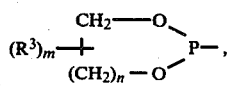

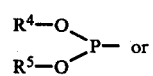

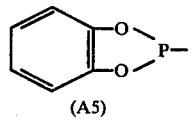

(A5)

wherein $R^3$ represents an alkyl group, $R^4$ and $R^5$ are the same or different, and each represent an alkyl group, n represents 1 or 2, m represents 0, 1, or 2, with an acyl halide in an aprotic solvent.

The specification of Belgian Pat. No. 809,110 and the cognate British patent applications Nos. 12788/75 and 26826/75 disclose a process for the preparation of penam and cephem derivatives by reacting a phosphite amide of 6-aminopenicillanic acid or 7-aminocephalosporanic acid with an acyl halide in an aprotic solvent. This reaction produces penam or cephem compounds in high yields. The reaction is proton catalysed, and the reaction rate may be controlled by varying the proton concentration in the reaction medium, for example by adding as a proton source varying amounts of an acid addition salt of a weak tertiary amine optionally in admixture with the weak tertiary amine itself. Examples of such amines are pyridine and N,N-dimethylaniline and examples of acid addition salts are hydrochlorides. The overall reaction proceeds with elimination of a phosphite halide, as exemplified in the following reaction scheme for the synthesis of the trimethylsilyl ester of amipicillin:

Scheme 1

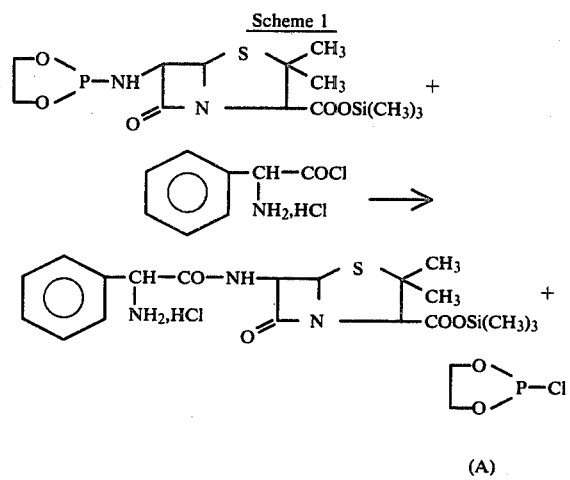

(A)

Phosphite halides, such as the compound having the formula A, while quite stable under aprotic conditions, react with hydroxylic reagents like water and alcohols. During synthesis, therefore, hydroxyl groups and similar substituents should be properly protected. Problems may also arise when a hydrolytic step is included in a synthesis of such sensitive compounds as penicillins and cephalosporins, unless the violent reaction between the phosphite halide and water is adequately controlled. Surprisingly, it has now been found that these obstacles may be overcome by adding a phosphite halide scavenger to the reaction mixture.

SUMMARY OF THE INVENTION

Thus, according to this invention, the reaction between the phosphite amide of the general formula I and an acyl halide in an aprotic solvent is carried out in the presence of a phosphite halide scavenger.

As mentioned above, $R^1$ may be a substituted alkyl or aralkyl group. Examples of substituted alkyl groups are 2,2,2-trichloroethyl, p-bromophenacyl, pivaloyloxymethyl, and phthalidyl groups. Examples of substituted aralkyl groups are benzhydryl and benzyl groups which optionally are substituted by a nitro group in the benzene ring. Examples of a metal organic group are trialkylsilyl and, preferably, trimethylsilyl groups. Throughout the present specification and claims, the term alkyl, when used alone or in combination with other groups, designates a straight or branched alkyl group, preferably containing at the most 6 carbon atoms, more preferred 4 carbon atoms, e.g. a methyl, ethyl, propyl, isopropyl, and tert.butyl group. Examples of groups having the formula A3 are 1,3,2-dioxaphospholan-2-yl and groups of the general formula A4 wherein $R^4$ and $R^5$ each represent an ethyl group.

It is preferred that the acyl halide to be used in the process according to the present invention has the general formula:

  (II), wherein $R^6$ represents a naphthyl group; a cycloalkyl group substituted with an amino group and optionally containing an oxygen or sulphur atom; a phenyl group substituted by one or more alkoxy group(s); a substituted heterocyclyl group; or a methyl group substituted with one or two of the following substituents: a phenoxy, amino, cyclohexyl group containing one or two unsaturated bond(s), a triazo, a substituted or non-substituted phenoxycarbonyl group, a substituted or non-substituted phenyl, alkyl, thienyl, cyano, hydroxy group, or a non-substituted or halogen substituted pyridylthio group, or corresponding groups containing a hydroxy or amino protecting group on a hydroxy or amino group, if any, and Hal represents halogen. Preferably $R^6$ is a 1-aminocyclohexyl, 4-aminotetrahydropyran-4-yl, 4-aminotetrahydrothiopyran-4-yl, 1-aminocyclopentyl, phenoxymethyl, 1-(1,4-cyclohexadienyl)aminomethyl, α-triazobenzyl, α-(2,3-dihydroinden-5-yloxycarbonyl)benzyl, α-aminobenzyl or a 3-phenyl-5-methyl-isooxazol-4-yl group which optionally is substituted with halogen in the 2- and 6-position of the phenyl group, a 2,6-dimethoxyphenyl, p-hydroxy-α-aminobenzyl, 1-phenoxypropyl, thien-2-ylmethyl, 1-naphthyl, 1-(thien-3-yl)aminomethyl, 1H-tetrazol-1-ylmethyl, or pyrid-4-ylthiomethyl group which optionally is substituted with halogen in the 2- and 6-position, a cyanomethyl, α-hydroxybenzyl, or p-(3,4,5,6-tetrahydropyrimidin-2-yl)phenylmethyl group, or corresponding groups containing a hydroxy or amino protecting group on a hydroxy or amino group, if any.

As mentioned above, $R^2$ may be a -S-Het group, wherein Het represents a heterocyclic group. Examples of such heterocyclic groups are tetrazole, 1,2,3-triazole, 1,3,4-thiadiazole, and alkyl or carboxyalkyl substituted tetrazole, 1,2,3-triazole, and 1,3,4-thiadiazole groups such as methyltetrazole, carboxymethyltetrazole, and 2-methyl-1,3,4-thiadiazole groups.

Throughout the present specification and claims, the term halogen, when used alone or in combination with other groups, designates bromine, chlorine, and fluorine, most preferred chlorine.

An example of a compound containing an amino protecting group is a compound of the formula II wherein $R^6$ contains a group of the formula $-NH_3^+Z^-$ wherein HZ is an organic or inorganic acid. Preferably, HZ represents HCl. An example of a hydroxy protecting group is a trialkylsilyl, preferably trimethylsilyl group, which means $R^6$ contains a p-trialkylsilyloxy, preferably p-trimethylsilyloxy group. It is also possible to use other compounds containing a protecting group, provided that said protecting group subsequently can be readily split off yielding the desired penam or cephem compound.

Examples of scavengers suitable for use in the process of the invention are epoxides and vinyl ethers which are capable of reacting quantitatively or almost quantitatively with the phosphite halide as demonstrated in Example 1, in which 2-chloro-1,3,2-dioxaphospholane and propylene oxide are used as reactants in a control reaction. This reaction may be illustrated by the following scheme:

Scheme 2

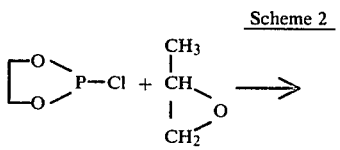

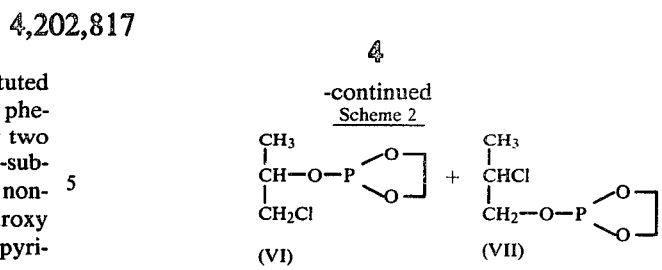

which, however, is merely illustrative, not restrictive as to the scope of the invention.

Since the phosphite halide scavenger does not interfere with the amide forming reaction according to Scheme 1, the presence of a scavenger such as an epoxide or a vinyl ether will permit the reaction to be performed also with a reactant carrying an unprotected hydroxyl group, such as D-(−)-p-hydroxyphenylglycylchloride,hydrochloride which is used in the preparation of p-hydroxyampicillin.

A preferred subclass of phosphite halide scavengers suitable for use in the process according to the present invention is compounds of the general formula:

$$R^7-Q-R^8 \qquad (III),$$

wherein Q represents a moiety of the formula

and $R^7$ and $R^8$ are the same or different and each represents hydrogen, a substituted or non-substituted alkyl group, or an aryl group, or $R^7$ and $R^8$ together with Q form a heterocyclic ring, with the proviso that any symbol $R^7$ or $R^8$ connected to the oxygen atom in the moiety Q of the formula —CH=CH—O— does not represent hydrogen.

A preferred subclass of compounds of the general formula III is compounds of the general formula:

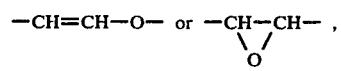

wherein $R^9$ represents hydrogen, a substituted or non-substituted alkyl group or an aryl group, and preferably compounds wherein $R^9$ represents a methyl, chloromethyl, or phenyl group.

A further preferred subclass of compounds of the general formula III is compounds of the general formula:

$$R^{11}-CH=CH-O-R^{10} \qquad (V),$$

wherein $R^{11}$ represents hydrogen or an alkyl group, and $R^{10}$ represents an alkyl group, or $R^{10}$ and $R^{11}$ together with the —CH=CH—O— moiety form a heterocyclic ring, and preferably compounds wherein $R^{11}$ represents hydrogen, and $R^{10}$ represents an ethyl or butyl group, or $R^{10}$ and $R^{11}$ together represent a trimethylene group.

It might have been expected that when the acylation of a phosphite amide with an acyl halide containing a free hydroxy group (e.g. when $R^6$ represents a p-hydroxy-α-aminobenzyl group) is performed even in the presence of an excess of a weekly basic tertiary amine, a reaction with the unprotected hydroxyl group would ensue, resulting in the production of a tertiary phosphite ester. The efficiency of the phosphite halide scavenger to block this reaction in the presence of a weak base, viz. N,N-dimethylaniline, is demonstrated in the following Example 9.

The process according to the present invention is further illustrated by the following non-limiting examples.

EXAMPLE 1

2-Chloro-1,3,2-dioxaphospholane (0.9 ml, 0.1 millimole) is dissolved in dry methylene chloride (5.6 ml) at room temperature, and propylene oxide (3.5 ml, 50 millimoles) is added. A slightly exothermic reaction ensues, producing a mixture of two compounds as shown by GLC. $^{31}$p-NMR spectra of the reaction mixture shows two signals at $\delta 32\ 143$ ppm and at $\delta = 134$ ppm and indicate that the two compounds formed have the formulae VI and VII, respectively. No signal from the starting material ($\delta = 168$ ppm) could be observed. Spectra were recorded at 36.43 MHz, and 85 percent phosphoric acid was used as an external standard.

Upon addition of water to the reaction mixture, chloride ions could not be detected by the addition of silver nitrate solution, but precipitation of metallic silver was observed.

The formation in a ratio of about 2:1 of the two propylene chlorohydrins corresponding to Compounds VI and VII stated in Scheme 2 was demonstrated by GLC.

EXAMPLE 2 p-Hydroxyampicillin.

Diisopropylamine (84 ml, 0.6 mole), dissolved in dry methylene chloride (400 ml) is cooled to 0° C., and 2-chloro-1,3,2-dioxaphospholane (27 ml, 0.3 mole) is added dropwise at this temperature. After 30 minutes the temperature is allowed to rise to room temperature and 6-aminopenicillanic acid (64.8 g, 0.3 mole) and trimethylchlorosilane (38 ml, 0.3 mole) are added. When the slightly exothermic reaction has subsided, the mixture is stirred for three hours, cooled to 0° C. and filtered to remove the precipitated amine hydrochloride. To the cooled filtrate pyridine hydrochloride (2.32 g, 20 millimoles), propylene oxide (70 ml, 1 mole) and D-(−)-p-hydroxyphenylglycylchloride, hydrochloride (54.5 g, 0.2 mole) are added with vigorous stirring. The reaction is completed after 40 minutes. The yield is estimated to be 94 percent by titration following hydrolysis by means of B. cereus penicillinase. $^{31}$p-NMR spectra of this solution showed the two signals at $\delta = 143$ and $\delta = 134$ mentioned in Example 1.

The reaction mixture is poured onto ice-water with vigorous stirring, while the pH of the mixture is adjusted to 2 with sodium hydroxide solution. After stirring for 30 minutes, the organic phase is removed, the aqueous phase washed twice with methylene chloride, and the product precipitated by adjusting the pH to 4.9 with aqueous ammonia solution. After two hours the product is isolated by filtration and washed on the filter with water. Yield: 69.2 g (82.5 percent) of crude material of 83 percent purity as estimated biologically against Sarcina lutea. Further purification may be performed by known methods.

EXAMPLE 3

A reaction mixture is prepared as described in Example 2 from 6-aminopenicillanic acid (3.18 g, 15 millimoles), D-(−)-p-hydroxyphenylglycylchloride,hydrochloride (2.72 g, 10 millimoles) and propylene oxide (3.5 ml, 50 millimoles) but omitting the addition of pyridine hydrochloride. This reaction is called reaction A.

In the same way another reaction mixture was prepared, this time with the addition of pyridine hydrochloride (116 mg, 1 millimole). This reaction is called reaction B.

These reactions were followed by enzymatic titration of the penicillin content at intervals:

| Time | Yield percent: | |
| --- | --- | --- |
| minutes | Reaction A | Reaction B |
| 5 | 3 | 47 |
| 15 | 18 | 80 |
| 35 | 65 | 90 |
| 60 | 77 | 95 |
| 90 | 85 | 95 |
| 120 | 90 | |

EXAMPLE 4

Two reaction mixtures were prepared as described in Example 3 B, except that the propylene oxide was replaced by dihydropyran (4.5 ml) and the amounts of pyridine hydrochloride were as follows:
Reaction A: 116 mg (1 millimole)
Reaction B: 1.74 g (15 millimoles)
The reactions were followed tritrimetrically:

| Time | Yield percent | |
| --- | --- | --- |
| | Reaction A | Reaction B |
| 5 minutes | 2 | 80 |
| 10 minutes | 15 | 80 |
| 60 minutes | 60 | 80 |
| 2 hours | 74 | |
| 3 hours | 85 | |
| 24 hours | 85 | |

EXAMPLE 5

A reaction mixture as described in Example 3 B was prepared except that the addition of propylene oxide was omitted. The amount of pyridine hydrochloride was 116 mg (1 millimole). The reaction was followed tritrimetrically:

| Time minutes | Yield percent |
| --- | --- |
| 3 | 66 |
| 6 | 68 |
| 15 | 44 |
| 30 | 31 |

EXAMPLE 6

A reaction mixture as described in Example 3 B was prepared, except that the propylene oxide was replaced by ethyl vinyl ether (4.8 ml). The yield was estimated tritrimetrically after 2 and 4 hours to be 77 percent.

EXAMPLE 7

In a reaction mixture as described in Example 2, the propylene oxide was replaced by 4 ml of epichlorohydrin (1-chloro-2,3-epoxypropane). The yield (obtained by titration) of amoxycillin was 90 percent after 45 minutes.

EXAMPLE 8

In a reaction mixture as described in Example 2, the propylene oxide was replaced by 10.5 ml of styrene oxide. The yield (obtained by titration) of amoxycillin was 85 percent after 45 minutes.

EXAMPLE 9

2.8 ml (20 millimoles) of diisopropylamine dissolved in 15 ml of dry methylene chloride was cooled to 0° C., and 0.9 ml (10 millimoles) of 2-chloro-1,3-dioxaphospholane dissolved in 5 ml of methylene chloride was added dropwise. After stirring for 30 minutes, the temperature was raised to 20° C., and 2.16 g of 6-aminopenicillanic acid were added, followed by 1.2 ml (10 millimoles) of trimethylchlorosilane. After stirring for 3 hours at room temperature the mixture was cooled to 0° C., and the precipitated diisopropylamine, hydrochloride was removed by filtration. The filtrate was cooled to −15° C., and 0.93 ml of a 2 N solution of N,N-dimethylaniline,hydrochloride in methylene chloride, 1.3 ml of N,N-dimethylaniline and 3.5 ml of propylene oxide were added, followed by 2.4 g (9 millimoles) of p-hydroxyphenylglycylchloride,hydrochloride. The cooling bath was removed, and the temperature raised to 15° C. during 10 minutes. After reacting for 30 minutes the above-mentioned compounds VI and VII were identified in the reaction mixture by gas chromatography. The yield, calculated against a reference standard solution, was 65%. The yield of penicillin, as estimated by enzymatic titration, was 70%.

We claim:

1. In a process for the preparation of penam or cephem derivatives by reacting a phosphite amide of the general formula:

$$Z-NH-CH-CH-S \atop \phantom{Z-NH-}CO-N-X \quad (I)$$

wherein X represents a group of the general formula:

$$\begin{array}{cc} CH_3 & -CH_2 \\ | & | \\ -C-CH_3 & C-CH_2R^2 \\ | & \| \\ -CH-COOR^1 & -C-COOR^1 \\ (A1) & (A2) \end{array} \quad \text{or}$$

wherein the carbon atom adjacent to the COOR$^1$ group is connected to the nitrogen atom, R$^1$ represents a conventional penam or cephem substituted or non-substituted alkyl or aralkyl group, or a metal organic group, R$^2$ represents a conventional penam or cephem group selected from hydrogen, an acetoxy group, or —S-Het, wherein Het represents a heterocyclic group, and Z represents a group having the formula:

$$(R^3)_m \begin{array}{c} CH_2-O \\ \phantom{xx} \diagdown \\ \phantom{xxx} P- \\ \phantom{xx} \diagup \\ (CH_2)_n-O \end{array} \quad \begin{array}{c} R^4-O \\ \diagdown \\ P- \\ \diagup \\ R^5-O \end{array} \text{ or } \begin{array}{c} \diagup O \diagdown \\ \phantom{x} P- \\ \diagdown O \diagup \end{array}$$

(A3) (A4) (A5)

wherein R$^3$ represents an alkyl group, R$^4$ and R$^5$ are the same or different, each representing an alkyl group, n represents 1 or 2, m represents 0, 1 or 2, with a p-hydroxyphenylglycyl halide or an acid addition salt thereof in an aprotic solvent, the improvement wherein the reaction is carried out in the presence of a proton donor and a phosphite halide scavenger, having the general formula:

$$R^7-Q-R^8 \quad (III),$$

wherein Q represents a moiety of the formula $$-C=CH-O- \quad \text{or} \quad -CH-CH- \atop \phantom{xxxxxxxxxxx} \diagdown O \diagup$$

and R$^7$ and R$^8$ are the same or different, each representing hydrogen, an alkyl group optionally substituted by a chlorine atom, or a phenyl group, or R$^7$ and R$^8$ together represent trimethylene, with the proviso that any symbol R$^7$ or R$^8$ connected to the oxygen atom in the moiety Q of the formula —CH═CH—O— does not represent hydrogen, to prevent the phosphite halide produced by the reaction from reacting with water or alcohol.

2. The process according to claim 1 wherein said scavenger has the general formula $$\begin{array}{c} R^9-CH \\ \phantom{xx} | \phantom{x} \diagdown O \\ \phantom{xx} CH_2 \diagup \end{array} \quad (IV),$$

wherein R$^9$ representa hydrogen, an alkyl group optionally substituted by a chlorine atom, or a phenyl group.

3. The process according to claim 2 wherein R$^9$ represents a methyl, chloromethyl, or phenyl group.

4. The process according to claim 1 wherein said scavenger has the general formula:

$$R^{11}-CH=CH-O-R^{10} \quad (V),$$

wherein R$^{11}$ represents hydrogen or an alkyl group, and R$^{10}$ represents an alkyl group, or R$^{10}$ and R$^{11}$ together represent a trimethylene group.

5. The process according to claim 4 wherein R$^{11}$ represents hydrogen, and R$^{10}$ represents an ethyl or butyl group.

6. The process according to claim 1 wherein R$^1$ represents a trialkylsilyl group.

7. The process according to claim 1 wherein R$^1$ represents a trimethylsilyl group.

8. The process according to claim 1 wherein the proton donor is an acid addition salt of a tertiary amine.

9. The process according to claim 1 wherein the proton donor is a mixture of a tertiary amine and an acid addition salt of a tertiary amine.

10. The process according to claim 1 wherein the proton donor is an acid addition salt of pyridine or N,N-dimethylaniline.

11. The process according to claim 1 wherein the proton donor is a hydrochloride of a tertiary amine.

12. The process according to claim 1 wherein a yield of 95% is obtained within 60 minutes.

13. The process according to claim 1 wherein X has the formula $$\begin{array}{c} CH_3 \\ | \\ -C-CH_3 \\ | \\ -CH-COOR^1 \end{array}$$

wherein R$^1$ represents a trimethylsilyl group, and wherein Z represents a 1,3,2-dioxaphospholan-2-yl group.

* * * * *